United States Patent [19]

Meloen et al.

[11] Patent Number: 5,885,966
[45] Date of Patent: Mar. 23, 1999

[54] PEPTIDE, IMMUNOGENIC COMPOSITION AND VACCINE OR MEDICAL PREPARATION, A METHOD TO IMMUNISE ANIMALS AGAINST THE HORMONE LHRH, AND ANALOGS OF THE LHRH TANDEM REPEAT PEPTIDE AND THEIR USE AS VACCINE

[75] Inventors: Robert Hans Meloen; Hendrica Berendina Oonk, both of Lelystad, Netherlands

[73] Assignee: DLO Instituut Voor Dierhouderij En Diergezondheid, Netherlands

[21] Appl. No.: 981,557

[22] PCT Filed: Jun. 6, 1996

[86] PCT No.: PCT/NL96/00223

§ 371 Date: Dec. 5, 1997

§ 102(e) Date: Dec. 5, 1997

[87] PCT Pub. No.: WO96/40755

PCT Pub. Date: Dec. 19, 1996

[51] Int. Cl.⁶ ............... A61K 38/00; C07K 5/00; C07K 7/00

[52] U.S. Cl. ............ 514/13; 530/402; 530/313; 424/185.1

[58] Field of Search .................. 514/13, 11, 10; 530/300, 313, 326, 402; 424/185.1

[56] References Cited

FOREIGN PATENT DOCUMENTS 9011298  10/1990  WIPO .............................. C07K 7/20

OTHER PUBLICATIONS

*Vaccine*, Meloeen et al., vol. 12, No. 8, 1994, pp. 741–746.

*Primary Examiner*—Avis M. Davenport
*Attorney, Agent, or Firm*—Trask, Britt & Rossa

[57] ABSTRACT

The invention relates to a modified tandem LHRH-peptide vaccine preparation in which the amino acid glycine at position (6) of one or both LHRH decapeptides that constitute the tandem unit is substituted by a dextrorotatory amino acid that contains a side chain to whicha carrier compound can be coupled. In addition, the tandem LHRH-peptide can be brought into a tandem-dimer form which is also suitable for producing a vaccine that is effective against LHRH (luteinizing hormone releasing hormone) also referred to as GnRH (gonadotropin-releasing hormone), for immunological castration, to inhibit or affect reproductive functions or to affect behaviour in vertebrates in general and in domesticated animals and man in particular.

15 Claims, No Drawings

PEPTIDE, IMMUNOGENIC COMPOSITION AND VACCINE OR MEDICAL PREPARATION, A METHOD TO IMMUNISE ANIMALS AGAINST THE HORMONE LHRH, AND ANALOGS OF THE LHRH TANDEM REPEAT PEPTIDE AND THEIR USE AS VACCINE

This invention relates to a peptide suitable for producing a vaccine effective against the Luteinising Hormone Releasing Hormone (LHRH, also referred to as Gonadotrophin Releasing Hormone, GnRH). The invention further relates to immunogenic compositions and vaccines or medicinal preparations (vaccines and pharmaceuticals) based on such a peptide and the use of such a vaccine or medicinal preparation in a method of immunizing a mammal against LHRH and thereby influencing reproductive or behavioral characteristics of that mammal and in a method of improving the meat quality of pigs.

LHRH is a small 10 amino acid long peptide (decapeptide) from the hypothalamus. The amino acid sequence (with, as usual, the amino terminal amino acid to the left and the carboxy terminal amino acid to the right) of LHRH is according to the formula in which the amino acids are coded with the three-letter code: pGlu-His-Trp-Ser-Tyr-Gly-Leu-Arg-Pro-Gly-NH$_2$, or in the one letter code according to the formula: #E H W S Y G L R P G@, #E is pyroglutamic acid and G@ is glycine amide.

LHRH acts at the hypophysis to cause an increase in release of biologically active FSH (follicle-stimulating hormone) and LH (luteinising hormone) in the blood, which in turn stimulate the development of the testes in the growing male animal and the synthesis of testicular steroids. In the growing female animal the development of the ovaries is stimulated and therein follicle development, synthesis of ovarian steroids and ovulation.

It is known that LHRH, if coupled to a carrier protein, can be used to vaccinate animals. Such a vaccination can be carried out for different reasons which are all connected with the natural function of the LHRH. As is known, a drastic reduction of LH and FSH in the blood inhibits the production of testicular steroids or androgens and sperm in the testis of the male and the formation of ovarian steroids or progestagens and estrogens and follicle maturation in the ovary of the female. Such a reduction of the amounts of androgens, progestagens and estrogens in the blood to a level comparable to the level obtainable by removing the testes or ovaries via castration can be achieved by effective immunization of the animal against LHRH. In male animals in many cases the testes then appear to develop slowly or not at all (no synthesis of androgens (male steroid hormones) and no formation of spermatozoa) and in female animals the activity of the ovaria appears to diminish (synthesis of estrogens and progestagens (female steroid hormones), ripening of follicles and ovulation are inhibited).

In veterinary medicine, 100% effective immunisation against LHRH could be used for the sterilisation of, e.g., small domestic animals such as male and female cats and dogs, or for the treatment of aggressiveness in male dogs and bulls, simply by vaccination instead of by drastic surgery such as castration or ovariectomy. Other conceivable reasons for immunisation against LHRH are to prevent heat in female animals, such as dogs, cats and cows, and restlessness in male animals, being fattened for slaughter. In human health care, immunisation against LHRH can be used in the treatment of prostate cancer and breast cancer and, if required in the treatment of some forms of pituitary carcinoma.

Another use of a vaccine against LHRH is in the field of stock breeding, particularly the fattening of pigs for slaughter. The meat of male, sexually mature pigs (boars) has a typical odour, the so-called boar taint or boar odour. In the sexually mature pig in the testes many C19-Δ16 steroids are formed which are stored in the fat tissue of the animal (Patterson, J. Sci. Food Agric. 19, 31–38 (1968); Brooks en Pearson, J. Anim. Sci. 62, 632–645 (1986); Claus, Zeitschrift. Tierzüchtg. Züchtungsbiol. 93, 38–47 (1976); Claus,. Acta Endocrinol. (Copenh.) 91, Suppl. 225, 432–433 (1979)). These steroids are mainly responsible for the formation of the disagreable urine-like odour when the meat is heated (Fuchs, Swedish J. Agric. Res. 1, 233–237 (1971); Bonneau, Livest. Prod. Sci. 9, 687–705 (1982)). Owing to this unpleasant odour, meat of male sexually mature pigs is hardly, if at all, suitable for consumption and unfit for export. Because about 10% of the male slaughter pigs are already sexually mature before the slaughter time, this potentially entails a great loss for the pig farming industry.

In order to control and prevent these losses, nearly all male piglets are castrated when they are young, with a surgical procedure that is generally executed without any form of anaesthesia. Apart from the animal unfriendly aspect of such a castration, castration also leads to infections, growth inhibition, and a final meat quality inferior to that of an intact animal (at least as long as that intact animal has not yet developed boar taint) (Walstra, Livest. Prod. Sci. 1, 187–96 (1974)).

An animal friendly alternative which in addition benefits meat quality consists in the reduction of the LHRH concentration at the pituitary of the young animal by means of immunisation against LHRH. This reduction in LHRH levels leads to a reduction in the concentrations of biologically active FSH and LH, which in turn will inhibit development of the testes in the growing animals and inhibit the synthesis of testicular steroids among which the C19-Δ16 steroids. Animal unfriendly castration becomes unnecessary: infections and growth inhibition are being prevented while the ultimate meat quality certainly is not less than after castration. In addition this method prevents the occurrence of boar taint in male pigs before slaughter time.

However, a strict requirement for a good vaccine against boar taint is that in all pigs development of the testes is being delayed to such an extent that in no case boar taint will occur before slaughter time, even not when tested in a very large population of pigs. The known vaccine preparations do not meet this requirement.

In the existing literature and previous patent applications regarding the anti-fertility properties of vaccines against LHRH, the results of vaccinations often appear to be variable, for instance, some vaccinated animals hardly, if at all, respond to the vaccination, or large doses in commercially unacceptable adjuvants are needed for the desired effect (Chaffaux et al., Recueil de Médicine Vétérinaire 161 (2), 133–145 (1985); Caraty et al., C. R. Acad. Sc. Paris, t. 303, Série III, No. 16, 673–676 (1986); Falvo et al., J. Anim. Sci. 63, 986–994 (1986); Goubau et al., Domest. Anim. Endocrinol. 6, 339–347 (1989a); Goubau et al., Theriogenology 32, 557–567 (1989b); Hoskinson et al, Austr. J. Biotech. 4, 166–170 (1990); Bonneau et al., J. Anim. Sci. 72, 14–20 (1994); U.S. Pat. No. 4,608,251; Int. patent appl. WO 88/05308). According to the literature data, it is not possible, using vaccination against LHRH, to block testis development in each individually immunized pig at a sufficiently early stage to entirely prevent the problem of boar odor. The percentage of success appears to lay between 20 and 80%. This is insufficient and renders the present generation LHRH-vaccines useless for farming practice.

The difficulty in preparing this type of vaccines probably is caused by the phenomenon of "tolerance". "Self" substances such as hormones are not recognized but indeed tolerated by the immune system. Normally no antibodies are being elicited against self substances. A successful vaccine therefore needs to use a substance sufficiently alike the hormone but at the same time sufficiently "foreign" to induce production of antibodies. Because these are mutually exclusive conditions it was not certain, until recently, if such substances could be prepared at all. One attempt to produce LHRH-like peptide vaccines consisted of the replacement of Gly at position 6 of the LHRH decapeptide by a dextrorotary amino acid (D-Tryp; Chaffaux et al., Recueil de Médicine Vétérinaire 161 (2), 133–145, 1985). It was, however, demonstrated that a vaccine preparation containing this modified LHRH-peptide performed even less well than the normal LHRH decapeptide (EP 0 464 124).

Recently, however, we have shown that it definitively is possible to elicit an effective antibody response in all individuals vaccinated against LHRH (Meloen et al., Vaccine 12, 741–746 (1994)). In these experiments pigs were vaccinated twice with an LHRH vaccine that departs from the "classical" type of LHRH vaccine (LHRH coupled to a carrier protein, in Freund's adjuvant), namely the tandem-LHRH vaccine (European patent nr. 0464124). According to the invention of the tandem-LHRH vaccine there is preferred a peptide which is characterised in that it comprises at least 2 LHRH sequences in tandem according to the general formula (with the amino terminal amino acid to the left and the carboxy terminal amino acid to the right) $Z^1$-Glx-His-Trp$^1$-Ser-Tyr-Gly-Leu-Arg-Pro[-Gly-X-Gln-His-Trp$^2$-Ser-Tyr-Gly-Leu-Arg-Pro]$_n$-Gly-Z$^2$, in which amino acids are designated according to the three-letter code, Trp$^1$ and Trp$^2$ are tryptophan (Trp) or formylated tryptophan (N$_{(indole)}$-formyl-tryptophan), n is a number having a value of at least 1, X is either a direct bond or a spacer group between the amino acids Gly and Gln, $Z^1$-Glx is either pGlu (pyroglutamic acid) or Gln having attached thereto a tail comprising one or more additional amino acids, and Gly-$Z^2$ is either Gly-NH$_2$ or Gly having attached thereto a tail comprising one or more additional amino acids. In this general formula, X may be a direct bond between the amino acids glycine and glutamine, i.e. these amino acids are interconnected directly without an intermediate link (via the normal peptide bond). The tandem-LHRH vaccine invention also comprises peptides in which the LHRH sequences are interconnected via spacers. The nature of the spacer group may greatly vary from one or more amino acids to a shorter or longer hydrocarbon chain and other compound groups or molecules. In the above general formula, $Z^1$-Glx preferably stands for pGlu (pyroglutamic acid), but can also stand for Gln having attached thereto a tail comprising one or more additional amino acids, e.g., to be used for coupling of the peptide to a carrier protein. In the above general formula, Gly-$Z^2$ stands for, e.g., Gly-NH$_2$, or Gly having attached thereto a tail comprising one or more additional amino acids, e.g., to be used for coupling of the peptide to a carrier protein. Preferably, Gly-$Z^2$ stands for Gly-Cys-NH$_2$, the C terminal cysteine being added in connection with a possible coupling of the peptide to a carrier protein.

More in particular, the tandem-LHRH vaccine invention provides a peptide which is characterised in that it comprises at least 2 LHRH sequences in tandem according to the general formula (with the amino terminal amino acid to the left and the carboxy terminal amino acid to the right) pGlu-His-Trp$^1$-Ser-Tyr-Gly-Leu-Arg-Pro[-Gly-Gln-His-Trp$^2$-Ser-Tyr-Gly-Leu-Arg-Pro]$_n$-Gly-Cys-NH$_2$, in which amino acids are indicated according to the three-letter code, Trp$^1$ and Trp$^2$ are either Trp or N-formyl-Trp, and n is a number having a value of at least 1.

This tandem-LHRH vaccine appeared to block completely testes growth and the development of steroid-producing (Leydig) cells in the testis. However, this vaccine appeared to have a number of disadvantages which made it less practical for use. One disadvantage was the need for a high dose to be applied in vaccination to make immunocastration successful, at least 1 mg per pig was needed to elicit the wanted respons, which makes it expensive to apply the vaccine on a large scale in the pig industry.

Another important disadvantage of this vaccine preparation is that this vaccine is so highly effective only in a composition with complete Freund's adjuvant. Use of this harsh adjuvant elicits many unwanted side effects such a difficulties in preparation and application due to its viscous nature, furthermore, the application itself can be very painful for the animal, and finally, remains of the adjuvant and the possible development of chronic inflammatory reactions to the adjuvant such as adjuvant related abscesses in the muscle at the injection site may decrease the meat quality of the injected animal.

The present invention, however, provides solutions to the undesired side effects of the above described vaccination against LHRH with the tandem-LHRH peptide preparation, without losing the beneficial advantages of the effective vaccination with a tandem-LHRH peptide in comparison with other existing vaccines directed against LHRH.

It was shown that the monomeric form of the tandem-LHRH vaccine with complete Freund's adjuvant but in total absence of the carrier protein KLH was fully effective in blocking testicle growth and boar odor in pigs and that dimeric forms of the tandem-LHRH vaccine applied without using the complete Freund's adjuvant but with the milder incomplete Freund's adjuvant instead resulted in fairly high efficacy. Surprisingly, it then also appeared that the tandem-principle applied to a variant of the LHRH molecule, namely with a substitution of the sixth amino acid Gly of the decapeptide by a dextrorotatory (D-) amino acid, D-Lys, after which the resulting peptide was coupled to a common carrier compound, (here ovalbumine was used), resulted in a vaccine that was very effective in several mild adjuvants, namely Specol and a double oil emulsion, and was furthermore also effective in low doses. Thus, whereas a vaccine using D-amino acid substitutions of Gly at position 6 of the original and single LHRH decapeptide with a D-amino acid did decrease the immunogenicity as compared to the original LHRH sequence, such substitutions with a D-amino acid applied to a tandem-LHRH vaccine were able to generate even more immunogenic LHRH vaccine preparations. It can further be expected that substitutions of Gly at position 6 of one or each the LHRH decapeptides that constitute the tandem unit with other dextrorotatory amino acid may also result in improving the vaccine. In addition, when using for example D-Lys as substituting amino acid, this allows for dimerisation or multimerisation of the tandem peptide without losing the possibility to conjugate the peptide composition to a carrier compound. Although the C-terminal cysteines can now be utilised for dimerisation via disulfide bond formation and thus would not be available for conjugation to a carrier compound any longer, the side chains of the amino acid substitutions still can be used for coupling to carrier compounds. Of course, substitutions with other amino acids that contain suitable side chains (such as D-Glu, but other possible substituting amino acids carrying suitable side chains are also known to the average expert) would also allow for additional coupling possibilities to a carrier compound.

[D-Lys⁶]-LHRH has been described as a superactive LHRH agonist (Seprodi et al., J. Med. Chem. 21, 276–280 (1978)) and among others has been used in LHRH-radioimmunoassays (Heber en Odell, Proc. Soc. Exp. Biol. Med. 158, 643–646 (1978)), as fluorescing ligand in LHRH-receptor research (Conn et al., J. Biol. Chem. 256, 1098–1100 (1981); Naor et al., J. Biol. Chem. 256, 3049–3052 (1981); Childs et al., Peptides 4, 549–555 (1983) ), and coupled to cytotoxic radicals to fight cancer growth (Szoke et al., Peptides 15, 359–366 (1994). [D-Lys⁶]-LHRH has not been applied before as LHRH-vaccine.

The present invention relates to a peptide or a peptide composition consisting of at least two LHRH sequences in tandem wherein the sixth amino acid Gly of the original LHRH decapeptide sequence is substituted with a D-amino acid. The Gly at position 6 may be substituted by a functional amino acid which in addition contains a side chain by which the LHRH tandem unit can be coupled to a carrier compound. This peptide may or may not be C-terminally amidated, depending on the peptide synthesis techniques used. In addition this peptide may be dimerised or multimerised, and then at least one of the tandem-LHRH-peptide sequences in the dimer or multimer will contain a functional amino acid substitution at position 6 of the original LHRH decapeptide.

The peptide or peptide composition according to the invention contains a consecutive sequence that can be described according to the following general formula:

in which * indicates possible replacement of Gly by a dextrorotatory amino acid which in addition contains a side chain by which the LHRH tandem unit can be coupled to a carrier compound.

A first feature of this invention is that in this peptide or peptide composition a possible replacement amino acid or amino acids can be substituted in which the sixth amino acid per LHRH decapeptide within the tandem unit, Gly, (thus in position 6 and/or 16 of the above general formula) is for instance replaced by an D-amino acid to generate a peptide that is different enough from the normal LHRH sequence to be recognised by the immune system without losing the proper immunogenicity.

Furthermore, a second feature of this invention is that individual tandem units are dimerised to further enhance its immunogenicity without losing the possibility to couple the peptide or peptide composition to a carrier compound protein. In this peptide or peptide composition such a dimerisation of the tandem units can for example take place via the carboxyl-terminus or via the amino-terminus, two tandem units may for instance be dimerised by means of a disulfide or thioether bridge. To this purpose the Cys at position 21 can be used, or Cys can be synthesised before the glutamic acid at position 1, but other methods to dimerise or multimerise the LHRH-tandem units can also be found in the prior art. In case the dimerisation or multimerisation results in the loss of accessible sites where a carrier compound can be conjugated, it is sufficient to restrict the choice of D-amino acids replacing Gly at position 6 and/or 16 to an amino acid with an appropriate side chain. Such a replacing amino acid can for example be D-Lys, D-Glu or another dextrorotatory amino acid containing a side chain that allows coupling to a carrier compound.

More in particular, a concrete example of such a preferred peptide according to the invention, a D-Lys⁶-tandem-LHRH dimer according to the following formula:

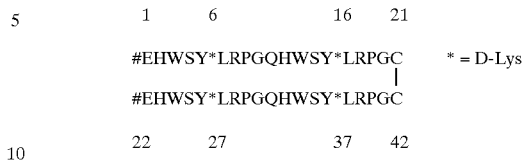

Another concrete example of such a preferred peptide according to the invention is a D-Glu⁶-tandem-LHRH dimer according to the following formula:

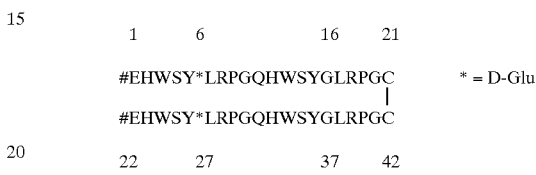

But other peptides or peptide compositions in which monomerised, dimerised or multimerised LHRH tandem units that contain D-amino acid substitutions at positions 6 and/or 16 and/or (as in the last two examples regarding dimeric forms) at positions 27 and/or 37 are also part of the invention, The invention further provided a composition which is characterized in the it comprises a peptide brought into an immunogenic form. As a skilled worker knows, there are different methods of bringing a substance which is in itself not immunogenic, into an immunogenic form. A first possibility is to couple a peptide according to the invention to a suitable carrier protein. In a tandem peptide, a cysteine at the N- or C-terminus can be suitably used for a chemical coupling. In the tandem-dimer peptide, coupling can also be performed using the plain or the modified side chain of D-lysine, D-glutamine, or any other modified amino acid replacing glycine at position 6 and/or 16 and/or 27 and/or 37. Those skilled in the art perfectly know what coupling methods and what carrier proteins are eligible. According to the invention there is preferred a composition which is characterized in that it comprises an immunogenic conjugate of a protein, such as ovalbumine, and a peptide or peptide composition according to the invention. Of course, the vaccine preparation according to the invention can be combined with at least one immunoadjuvant. Suitable immuno-adjuvants are known to those skilled in the art. A preferred adjuvant according to the invention can be Specol or a double oil emulsion, but other adjuvants that elicit no or only mild side-reactions can be used as well. The invention can be used in methods for immunising individuals selected from a wide range of vertebrates, but more in particular mammals, against LHRH. Immunisation against LHRH could for instance be used for the sterilisation of, e.g., small domestic animals such as male and female cats and dogs, or for the treatment of aggressiveness in male dogs and bulls. Other conceivable reasons of immunisation against LHRH with the present invention are preventing heat in female animals, such as dogs, cats and cows, and preventing or treating restlessness in male animals, being fattened for slaughter. In human health care, immunisation against LHRH can be used in the treatment of prostate cancer and breast cancer and, if required, in the treatment of some forms of pituitary carcinoma.

A preferred embodiment is a method of improving the meat quality of pigs, wherein the pigs are vaccinated with such a vaccine preparation according the invention. The invention is illustrated in the following experimental part.

EXAMPLES

Successful vaccination of boars is defined as testis weight at slaughter of less than 150 gram. The aim is visibly small testes in all animals within a treatment group. Testis weight appears to be directly correlated to the production of testosterone and of boar taint steroids. When testis weight is less than 60 grams the testes histologically were completely inactive (Meloen et al., Vaccine 12, 741–746 (1994)) and no testosterone in the serum could be detected. We have described that an excellent correlation exists between size and particularly weight of the testes and the level of androstenone in backfat (Oonk et al., Livest. Prod. Sci. 42, 63–71 (1995)). It appears that testes of immunized animals weighing less than 150 gram are a clear indication for the absence of boar taint. Androstenone in backfat was usually present in undetectably low concentrations, but if present was always lower than 0.5 µg/g backfat. This value in the literature is referred to as safe lower limit for the possible perception of boar taint although others report 1 µg/g backfat as sufficiently low. We take the lowest value as lower limit, below which we consider a pig as successfully immunocastrated. This relation is based on measurements in more than 100 pigs. Testicle weights of control animals in our experiments appeared to be within 200 and 350 grams. Finally feed conversion and meat/fat ratio appeared to be improved in immunocastrates compared to barrows (surgically castrated at young age).

METHODS

Peptide syntheses were performed on an ABI 430A peptide synthesizer using FastMoc cycles on a 0.25 mmole scale with cycle times of about 60 min (Fields CG, Lloyd DH, Macdonald RL, Otteson KM, Noble RL HBTU activation for automated Fmoc solid-phase peptide synthesis. Peptide Research 4, 95–101 (1991); User Bulletin #32, Applied Biosystems (1990)).

Peptide purification: The purifications were carried out using a Waters PrepLC4000 system, equipped with a Waters PrepPak Cartridge (25 mm×100 mm) filled with Delta-Pak C18 (15 µm, 100A) material and a guard column.

For analytical HPLC, we used two Waters pumps model 510, a Waters gradient controller model 680, a Waters autoinjector model WISP 712, and a Waters photodiode array detector model 991. The products were analyzed in a linear gradient from water with 0.1% TFA to 60% acetonitril in water with 0.1% TFA in 60 min on a Waters Delta Pak C18-100A (3.9×150 mm, 5 µm) column at 1 ml/min at 215 nm. All products were >95% pure according to the peak surface.

Amino acid analysis was done with the Waters PicoTag system. The results were in agreement with the expected values according to the amino acid sequences.

Dimerization procedure: The product was dimerized by dissolving the product in a 20% dimethylsulfoxide in water. The pH should be adjusted to 5–6 with 1% or 2% $NH_4HCO_3$. The solution should stay clear. Too high pH can be corrected with 1–10% acetic acid. Stir at room temperature for at least 5 h. The product was purified directly using HPLC.

Conjugation of D-Lys$^6$-tandem-dimer to ovalbumin: [Weight equivalents to be used: 1 mg of ovalbumin and 1 mg of D-Lys$^6$-tandem-dimer is coupled using 10 mg of ECDI in milliQ-water]. First both the peptide and the ovalbumin are dissolved in milliQ-water (A=peptide solution; B=ovalbumin solution). A and B are mixed well. Next a 10× excess, based on weight equivalents, of carbodiimide (ECDI) is dissolved in milliQ water (C =ECDI solution). Subsequently C is slowly added to the A+B solution under continuous stirring. After 6 h the product is dialyzed (MW cut-off 10,000) against water.

Determination of the loading: The loading is calculated from comparative amino acid analysis of the conjugate and the separate peptide and carrier protein. According to the amino acid analyses the conjugates contain approximately 0.5 mg peptide per mg ovalbumin.

Vaccine preparation: Vaccines were prepared by mixing peptide with adjuvant (see details at Specol).

Adjuvants tested were complete Freund's adjuvant (CFA), incomplete Freund's adjuvant (IFA), Specol oil, and double oil emulsion (d.o.e.).

CFA or IFA was mixed 1:1 with the peptide solution to a stable emulsion.

Double oil emulsion (W/O/W):
  10 parts first waterphase: antigen in PBS (Phosphate Buffered Saline).
  11 parts oil phase: Marcol 52 (Esso) with 10% mannide monooleate ("Arlacel").
  10 parts second waterphase: PBS with 2% Montanox 80 (=Tween 80).

Specol (Special Oil Phase) is a product suitable for production of water-in-oil emulsions for research purposes. Composition: Per 10 ml: 0.453 g Tween85 (ICI), 0.532 g Span85 (ICI), 9 ml Marcol 52 (Esso Belgium).

Preparation of emulsions in Specol: Mix 4 parts of the waterphase containing the antigen with 5 parts Specol (v/v) adding the waterphase very slowly to the oil phase (Specol) while vigorously mixing with e.g. an ultraturrax (vortexing is too mild). Prevent as much as possible the introduction of air. Use clean glassware free of detergents. Storage: Specol is preferably stored between 4°–8° C. (References: B. A. Bokhout et al., Vet. Immunol. Immunopathol. 2, 491–500 (1981); W. Hall et al., Vet. Immunol. Immunopathol. 22, 175–186 (1989); W. J. A. Boersma et al., Res. Immunol. 143, 503–511(1992)).

Vaccination protocol: For each vaccine, and per animal, 1 mg of peptide (as calculated from the loading), or a lower amount as indicated, prepared as described above, was dissolved in 1 ml phosphate buffered saline (PBS) and emulsified with the indicated adjuvant. Intact male pigs were approximately 10 weeks of age at the start of the experiment, when they received the first vaccination. The booster administered 8 weeks after the first vaccination had the same composition.

Evaluation: The size of the pig's testicles was measured externally using calipers. From approximately 12 weeks after the first vaccination the size of the testicles does not increase further (or even diminishes) in pigs with a lowered concentration of LHRH. Serum samples were taken for determination of anti-LHRH-titers and testosterone. Antibodies to GnRH were determined by binding of serial dilutions of the pig antisera to $^{125}$LHRH. Animals were slaughtered 16 weeks after the first vaccination. After slaughter testes were weighed and a backfat sample was taken for determination of the boar taint steroid androstenone using an ELISA (Ridascreen). Furthermore meat quality was judged.

EXPERIMENT 1

In these experiments different peptide constructs have been tested in unconjugated form. Each peptide was administered twice at the age of 10 and 18 weeks in a quantity of 1 mg using IFA as adjuvant. Tested constructs were carboxy-terminal dimerised LHRH-monomer, carboxy-terminal dimerised LHRH-tandem, amino-terminal dimerised LHRH-tandem, carboxy-terminal dimerised [D-Nal(2)⁶]-LHRH (Nafarelin®)-monomer, carboxy-terminal dimerised [D-Nal(2)⁶]-LHRH (Nafarelin®)-tandem, carboxy-terminal dimerised [D-Lys⁶]-LHRH-monomer and carboxy-terminal dimerised [D-Lys⁶]-LHRH-tandem.

1) Peptide formula of C-monomer-LHRH-dimer:

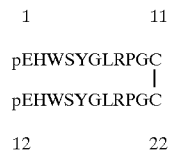

2) Peptide formula of C-tandem-LHRH-dimer:

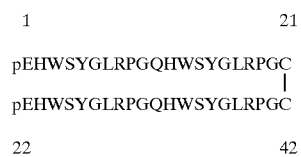

3) Peptide formula of N-tandem-LHRH-dimer:

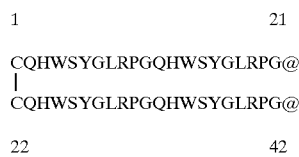

4) Peptide formula of [D-Nal(2)⁶]-monomer-LHRH-dimer:

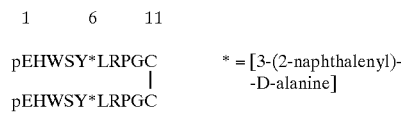

5) Peptide formula of [D-Nal(2)⁶]-tandem-LHRH-dimer:

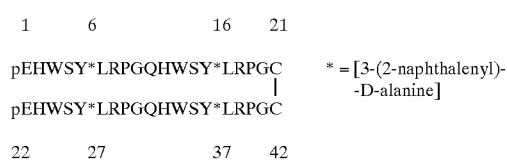

6) Peptide formula of [D-Lys⁶]-monomer-LHRH-dimer:

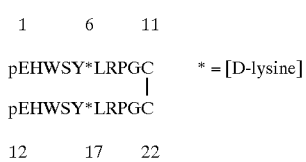

7) Peptide formula of [D-Lys⁶]-tandem-LHRH-dimer:

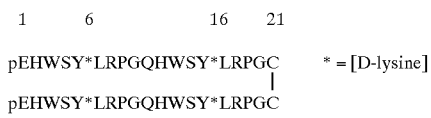

| Antigen | number of pigs with testis weight <150 g/group size | testis weight (means ± s.d.) |
|---|---|---|
| 1) C-monomer-LHRH-dimer | 0/7 | 294 ± 44 |
| 2) C-tandem-LHRH-dimer | 5/7 | 92 ± 105 |
| 3) N-tandem-LHRH-dimer | 6/7 | 88 ± 57 |
| 3) N-tandem-LHRH-dimer | 6/8 | 72 ± 89 |
| 4) [D-Nal(2)⁶]-monomer-LHRH-dimer | 2/7 | 177 ± 69 |
| 5) [D-Nal(2)⁶]-tandem-LHRH-dimer | 0/7 | 248 ± 56 |
| 6) [D-Lys⁶]-monomer-LHRH-dimer | 2/7 | 190 ± 44 |
| 7) [D-Lys⁶]-tandem-LHRH-dimer | 5/7 | 103 ± 102 |

In group 2, 3, and 7 70–80% of the animals appeared to be successfully immunocastrated. In these responders the highest measured testis weight was 86 g, whereas the non-responders had testis weights of 193 g or higher. From these results it appears that replacement of Complete Freund's Adjuvant by Incomplete Freund's Adjuvant in a formula with an unconjugated peptide leads to loss of effectivity. Furthermore, it particularly appears firstly that the tandem principle is essential for the activity of the vaccine, secondly that dimerisation can take place via the carboxy- or via the aminoterminus and thirdly that not every amino acid substitution is allowed, in view of the inefficiency of the Nafarelin®-analog as a vaccine.

EXPERIMENT 2

The already known successful vaccine based on the tandem-LHRH peptide coupled to keyhole limpet hemocyanine (KLH) in CFA for the first and IFA for the second vaccination was tested without conjugation to a carrier protein, in single and dimerised form, in CFA/IFA and in 2×IFA, and in a dose of 1 mg and 100 µg. Pigs were vaccinated 2× at 10 and 18 weeks of age.

1) Peptide formula of Tandem-LHRH:

2) Peptide formula of Tandem-LHRH-dimer:

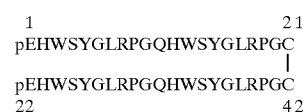

| Antigen | adjuvant | dose | number of pigs with testis weight <150 g/group size | testis weight (means ± s.d.) | LHRH-Ab titer at 8 wpv |
|---|---|---|---|---|---|
| 1) Tandem-LHRH | CFA/IFA | 1 mg | 6/6 | 38 ± 23 | |
| 1) Tandem-LHRH | CFA/IFA | 1 mg | 6/6 | 24 ± 6 | |
| 1) Tandem-LHRH | CFA/IFA | 1 mg | 6/6 | 41 ± 27 | |
| 1) Tandem-LHRH | CFA/IFA | 1 mg | 11/11 | 39 ± 14 | 17.8 ± 11.5 |
| 2) Tandem-LHRH-dimer, | CFA/IFA | 1 mg | 10/11 | 67 ± 64 | 16.7 ± 5.9 |
| 1) Tandem-LHRH | 2 × IFA | 1 mg | 5/13 | 159 ± 108 | 10.8 ± 8.4 |
| 2) Tandem-LHRH-dimer | 2 × IFA | 1 mg | 6/13 | 154 ± 95 | 8.7 ± 6.8 |
| 1) Tandem-LHRH | CFA/IFA | 100 μg | 7/12 | 121 ± 92 | 12.6 ± 5.9 |
| 2) Tandem-LHRH-dimer, | CFA/IFA | 100 μg | 6/12 | 132 ± 86 | 9.8 ± 5.2 |
| 1) Tandem-LHRH | 2 × IFA | 100 μg | 5/13 | 172 ± 92 | 3.5 ± 4.6 |
| 2) Tandem-LHRH-dimer | 2 × IFA | 100 μg | 1/13 | 220 ± 55 | 4.6 ± 5.4 |

The Tandem-LHRH vaccine in single or dimerised form appears to be virtually completely effective, even in complete absence of the carrier protein KLH in blocking testis growth and boar taint in pigs. However, an important disadvantage of this vaccine is that the very high effectivity is achieved only in a composition with complete Freund's adjuvant and in a high dose. In addition, reasonable anti-LHRH Ab titers (expressed as % binding of sera taken at 8 weeks postvaccination), were achieved only with tandem-LHRH or tandem-LHRH dimer in CFA/IFA at 1 mg dose.

EXPERIMENT 3

The effect of conjugation to a carrier protein was tested in combination with the replacement of IFA by the milder adjuvants Specol and double oil emulsion (d.o.e.). The dimerised tandem-LHRH-peptide with a replacement of Glycine by D-Lysine at positions 6, 16, 27 and 37 was conjugated to ovalbumin and emulsified in two different adjuvants, Specol and double oil emulsion. Pigs were vaccinated 2×, 10 and 18 weeks old, with 1 mg peptide-conjugate in adjuvant. The coupling efficiency is 50%, therefore the amount of antigen administered in reality is 500 μg.

Peptide formula of [D-Lys$^6$]-tandem-LHRH-dimer:

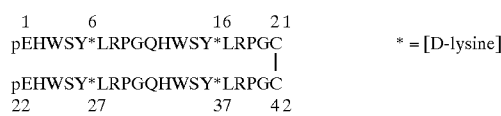

```
 1        6          16     21
pEHWSY*LRPGQHWSY*LRPGC           * = [D-lysine]
                     |
pEHWSY*LRPGQHWSY*LRPGC
 22       27         37     42
```

| Antigen | number of pigs with testis weight <150 g/group size | testis weight (means ± s.d.) |
|---|---|---|
| 1) [D-Lys$^6$]-tandem-LHRH-dimer-ova in Specol | 9/9 | 19 ± 12 |
| 2) [D-Lys$^6$]-tandem-LHRH-dimer-ova in d.o.e. | 8/8 | 43 ± 46 |

Conjugation to a commonly used carrier protein strongly improves the effectivity of the vaccine, even when a very mild adjuvant is being used.

EXPERIMENT 4

Subsequently in a number of experiments we tested to what extent the dose administered could be lowered. The peptide antigen was [D-Lys$^6$]-tandem-LHRH-dimer. This was coupled to ovalbumin and the conjugate was administered as emulsion in the adjuvant Specol. Pigs were vaccinated 2× at 10 and 18 weeks of age.

| Dose (μg conjugate) | number of pigs with testis weight <150 g/group size | testis weight (mean ± s.d.) | LHRH titer at 12 wpv |
|---|---|---|---|
| A. 1000 | 9/9 | 19 ± 12 | 46.5 ± 5.1 |
| B. 1000 | 8/8 | 43 ± 46 | 28.7 ± 13.0 |
| C. 1000 | 7/8 | 60 ± 62 | 44.1 ± 11.4 |
| D. 900 | 11/11 | 46 ± 38 | 24.4 ± 4.4 |
| C. 500 | 7/9 | 65 ± 69 | 36.3 ± 14.3 |
| D. 300 | 11/11 | 29 ± 18 | 28.0 ± 3.2 |
| E. 300 | 15/15 | 24 ± 18 | 35.3 ± 4.2 |
| C. 250 | 9/9 | 32 ± 12 | 45.1 ± 8.6 |
| C. 125 | 8/8 | 42 ± 42 | 44.9 ± 12.0 |
| F. 125 | 12/12 | 35 ± 37 | 27.8 ± 3.6 |
| G. 125 | 10/10 | 21 ± 12 | 26.5 ± 3.1 |
| H. 125 | 6/6 | 12 ± 2 | n.d. |
| K. 125 | 7/7 | 31 ± 22 | 29.5 ± 5.1 |
| D. 100 | 9/10 | 62 ± 58 | 23.2 ± 6.7 |
| D. 30 | 10/11 | 53 ± 65 | 25.6 ± 7.4 |
| E. 30 | 13/15 | 61 ± 75 | 32.5 ± 5.2 |
| D. 10 | 9/11 | 78 ± 86 | 22.9 ± 7.8 |
| E. 3 | 6/15 | 207 ± 117 | 21.3 ± 9.7 |

Using the [D-Lys$^6$]-tandem-LHRH-dimer-ovalbumin conjugate in Specol a marked reduction of vaccine dose needed can be achieved. In 43 pigs vaccinated with 125 μg conjugate (=62.5 μg peptide) the effectivity was 100%. In the backfat of pigs with testes smaller than 150 g in no occasion more than 0.5 μg androstenone/g backfat has been measured (Oonk et al., Livest. Prod. Sci. 42, 63–71 (1995)); in most cases the androstenone concentrations even are below the detection level in the ELISA (0.111 μg/g backfat). With doses of 10–100 μg conjugate there is an increased risk for non-responders, and doses lower than 10 μg are not effective. Anti-LHRH antibody titers are comparable only within an experiment. Results clearly show that low doses of vaccine are able to elicit similar titers as high doses, in contrast to the results obtained using the tandem-LHRH or tandem-LHRH-dimer. Within an experiment, lower average titers and larger standard deviations result from the contribution from pigs, not fully responsive or unresponsive to the vaccine.

EXPERIMENT 5

In control groups of intact boars testicle weights and androstenone have been determined.

| | number | testis weight (means ± s.d.) | androstenone (μg/g backfat) |
|---|---|---|---|
| 1. | 10 | 217 ± 38 | 0.68 ± 0.42 |
| 2. | 6 | 233 ± 41 | 2.04 ± 1.55 |
| 3. | 5 | 231 ± 58 | 2.05 ± 0.70 |

As reported before in Oonk et al., Livest. Prod. Sci. 42, 63–71 (1995) the androstenone concentration varies strongly in individual intact adult male pigs.

We claim:

1. A peptide that comprises at least two contiguous LHRH decapeptide sequences wherein the amino acid glycine at position 6 of at least one of the constituting LHRH decapeptides is replaced by a dextrorotatory amino acid with a side chain that can be coupled to a carrier compound.

2. A peptide according to claim 1 characterised in that it comprises an amino acid sequence that comprises the structure:

```
  1     6         16   21
#EHWSY*LRPGQHWSY*LRPGC
``` wherein the amino acid * at position 6 or 16 is a dextrorotatory amino acid with a side chain that can be coupled to a carrier compound and the other amino acid * is either glycine or a dextrorotatory amino acid with a side chain that can be coupled to a carrier compound.

3. Peptides according to claim 1 that are dimerised or multimerised.

4. A peptide according to claim 3 and comprising the structure:

```
  1     6         16   21
#EHWSY*LRPGQHWSY*LRPGC
                    |
#EHWSY*LRPGQHWSY*LRPGC
 22    27         37   42
``` wherein the amino acid * at position 6 or 16 or 27 or 37 is D-lysine or D-glutamine or another dextrorotatory amino acid with a side chain that can be coupled to a carrier compound and the other amino acid * is either glycine or D-lysine or D-glutamine or another dextrorotatory amino acid with a side chain that can be coupled to a carrier compound.

5. A peptide according to claim 3 and having the structure:

```
  1      6          16    21
#CQHWSY*LRPGQHWSY*LRPGC
                     |
#CQHWSY*LRPGQHWSY*LRPGC
 22     27          37    42
``` wherein the amino acid * at position 6 or 16 or 27 or 37 is D-lysine or D-glutamine or another dextrorotatory amino acid with a side chain that can be coupled to a carrier compound and the other amino acid * is either glycine or D-lysine or D-glutamine or another dextrorotatory amino acid with a side chain that can be coupled to a carrier compound.

6. A composition in which a peptide in accordance with claim 1 is coupled to a carrier compound.

7. A composition in accordance with claim 6 wherein the carrier compound is a protein.

8. A composition in accordance with claim 7 wherein the carrier compound is KLH or ovalbumin.

9. A composition in accordance with claims 1 additionally comprising a mild adjuvant.

10. A composition in accordance with claim 9 wherein the mild adjuvant is an oil phase of a water-in-oil emulsion or a double oil emulsion.

11. A vaccine comprising a composition in accordance to claim 1.

12. A method for inoculating an animal with a vaccine according to claim 11.

13. A method for inoculating an animal with a vaccine according to claim 11 wherein the effective amount is less than about 1 mg.

14. A method to effect one or more reproductive or behavioural characteristics of an animal, characterized in that said animal is vaccinated in accordance with claim 12.

15. A method to immunocastrate a pig, characterized in that said pig is vaccinated in accordance with claim 12.

* * * * *